United States Patent
Wu et al.

(10) Patent No.: US 11,247,200 B2
(45) Date of Patent: Feb. 15, 2022

(54) CARBON NITRIDE-BASED PHOTOCATALYST AND PREPARATION METHOD THEREOF

(71) Applicant: CHINA UNIVERSITY OF PETROLEUM (EAST CHINA), Qingdao (CN)

(72) Inventors: Wenting Wu, Qingdao (CN); Congcong Han, Qingdao (CN); Mingbo Wu, Qingdao (CN); Zhongtao Li, Qingdao (CN); Qinggang Zhang, Qingdao (CN)

(73) Assignee: CHINA UNIVERSITY OF PETROLEUM (EAST CHINA), Qingdao (CN)

( * ) Notice: Subject to any disclaimer, the term of this patent is extended or adjusted under 35 U.S.C. 154(b) by 192 days.

(21) Appl. No.: 16/487,177

(22) PCT Filed: Jul. 3, 2017

(86) PCT No.: PCT/CN2017/091479
§ 371 (c)(1),
(2) Date: Aug. 20, 2019

(87) PCT Pub. No.: WO2018/161482
PCT Pub. Date: Sep. 13, 2018

(65) Prior Publication Data
US 2020/0055036 A1 Feb. 20, 2020

(30) Foreign Application Priority Data
Mar. 6, 2017 (CN) .......................... 201710129107.X

(51) Int. Cl.
B01J 31/02 (2006.01)
B01J 35/00 (2006.01)

(52) U.S. Cl.
CPC ......... *B01J 31/0247* (2013.01); *B01J 35/004* (2013.01)

(58) Field of Classification Search
None
See application file for complete search history.

(56) References Cited

FOREIGN PATENT DOCUMENTS

CN 106902876 6/2017

OTHER PUBLICATIONS

International search report dated Dec. 14, 2017 from corresponding application No. PCT/CN2017/091479.
Written Opinion dated Dec. 14, 2017 from corresponding application No. PCT/CN2017/091479.

*Primary Examiner* — Yun Qian
(74) *Attorney, Agent, or Firm* — Hauptman Ham, LLP

(57) ABSTRACT

The present invention provides a carbon nitride-based photocatalyst and a preparation method thereof. The photocatalyst is prepared by reaction of melem with 3,3',4,4'-benzophenonetetracarboxylic dianhydride. The photocatalyst according to an embodiment of the present invention achieves energy level matching in structure between the melem structure and the 3,3',4,4'-benzophenonetetracarboxylic dianhydride, reduces a singlet-triplet energy gap ($\Delta E_{ST}$), promotes an intersystem crossing process, thereby enhancing the singlet oxygen production and improving the selective photocatalytic oxidation ability.

10 Claims, 3 Drawing Sheets

CARBON NITRIDE-BASED PHOTOCATALYST AND PREPARATION METHOD THEREOF

RELATED APPLICATIONS

The present application is a National Phase of International Application Number PCT/CN2017/091479, filed Jul. 3, 2017, and claims the priority of China Application No. 201710129107.X, filed Mar. 6, 2017.

TECHNICAL FIELD

This invention relates to the field of carbon material science, and specifically to a photocatalyst, and particularly to a high-efficiency selective carbon nitride-based photocatalyst and a preparation method thereof.

BACKGROUND

As a simple way to obtain complex organic oxidation products and to store solar energy into chemical energy, a high-efficiency selective photocatalytic oxidation provides a support for sustainable energy utilization. Reactive oxygen species with high reactivity and oxidizability play important roles in the high-efficiency selective photocatalytic oxidation process, where a singlet oxygen ($^1O_2$) has been proven to be an effective reactive oxygen species for many selective organic syntheses. At present, a series of reactions using $^1O_2$ as oxidant has been extensively studied, including selective sulfonation oxidation, selective oxidation of primary alcohol to aldehyde, and transformation of anthracene derivatives into anthraquinones. However, ground state oxygen ($^3O_2$) cannot directly produce $^1O_2$ by absorbing light due to the spin forbidden limitation, and therefore the photocatalysts are highly required.

In the past, the research of conventional photocatalysts were usually based on transition metal complexes (Pt(II), Ir(III), Ru(II), etc.) or some organic chromophores containing I or Br, since heavy atoms were proved to enhance spin orbital coupling (SOC). However, these compounds have small molar absorption coefficients in the visible-light spectrum and thus are poor in the utilization of visible light, thereby limiting their practical application. In recent years, conjugated polymers without heavy atoms have shown an attractive prospect in the production of $^1O_2$, therefore the carbon nitride ($C_3N_4$) with a conjugated structure has received great attention. However, the biggest disadvantage of the conjugated polymers is that the intersystem crossing (ISC) process is quite limited, which prevents the conversion of singlet excitons into triplet excitons. In this way, the $^1O_2$ production is essentially limited.

SUMMARY

An embodiment of the invention provides a carbon nitride-based photocatalyst with the following structure:

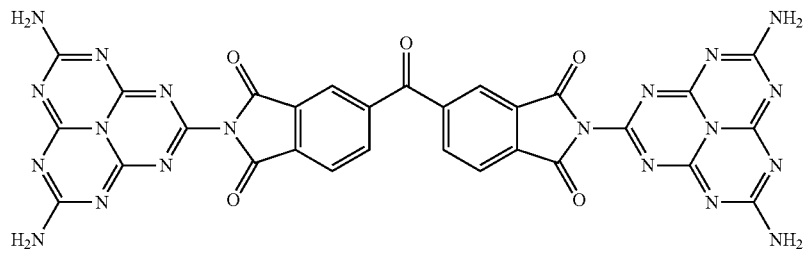 [SMILES: NC1=NC2=NC(N)=NC3=NC(N4C(=O)c5ccc(C(=O)c6ccc7c(c6)C(=O)N(C6=NC8=NC(N)=NC9=NC(N)=NC(=N6)N98)C7=O)cc5C4=O)=NC(=N1)N23]

Another embodiment of the invention provides a carbon nitride-based photocatalyst prepared by reacting melem with 3,3',4,4'-benzophenonetetracarboxylic dianhydride.

Another embodiment of the invention provides a method for preparing a carbon nitride-based photocatalyst, including:

preparing melem by polymerization of melamine; and preparing carbon nitride-based photocatalyst by reacting melem with 3,3',4,4'-benzophenonetetracarboxylic dianhydride.

An embodiment of the present invention provides a method for preparing a carbon nitride-based photocatalyst by introducing 3,3',4,4'-benzophenonetetracarboxylic dianhydride (BTDA) containing a ketone carbonyl group on the basis of the melem with a tris-triazine structure;

The specific preparation method includes the following steps:

(1) A certain amount of melamine was weighed and placed evenly at the bottom of a crucible. The crucible was then placed in a muffle furnace, and then heated to 425° C. at a heating rate of 1.77 K/min, and kept at this temperature for 4 h. After cooling, the crucible was taken out from the muffle furnace to obtain a pale yellow solid.

(2) The obtained solid was stirred in an appropriate amount of hot water (70° C.) for 15 min, vacuum-filtered three times, the obtained solid was dried in a vacuum drying oven to get melem.

(3) The melem and the 3,3',4,4'-benzophenonetetracarboxylic dianhydride were placed in a quartz mortar and thoroughly ground to mix them evenly. The ground mixture was placed in a quartz boat and the quartz boat was placed in a tube furnace for heating. The gas in the quartz tube was replaced with nitrogen before heating to evacuate air, and the nitrogen was always supplied during the heating. The tube furnace was heated to 300° C. at a heating rate of 5 K/min, and kept at this temperature for 4 h. After cooling, the sample was taken out of the tube furnace to obtain a solid.

(4) The obtained solid was washed three times with N,N-dimethylformamide and ethanol, through vacuum-filtration respectively, and the resulting solid was dried in a vacuum oven to obtain a final product.

The embodiment of the present invention provides a method for simply preparing a carbon nitride-based high-efficiency selective photocatalyst, in which 3,3',4,4'-benzophenonetetracarboxylic dianhydride with a long triplet lifetime is creatively introduced on the basis of melem (a tris-triazine structure). Their energy level matching can be achieved so that a singlet-triplet energy gap ($\Delta E_{ST}$) is reduced and an intersystem crossing process is promoted, which is conducive to the production of singlet oxygen and the enhancement of its selective photocatalytic oxidation ability. The most important feature of the present invention includes no complicated pretreatment and purification treatment to carry out, cheaply available raw material, simple and fast preparation process with environmental protection, and easy achievement for batch preparation of high-efficiency selective photocatalyst. The specific preparation method is described below.

(1) A certain amount of melamine was weighed and placed evenly at the bottom of the crucible. The crucible was then placed in a muffle furnace with, heated to 425° C. at a heating rate of 1.77 K/min, and held at this temperature for 4 h. After cooling, the crucible was taken out from the muffle furnace, the obtained pale yellow solid was stirred in an appropriate amount of hot water for a certain period of time and vacuum-filtered three times, and then the obtained solid was dried in a vacuum drying oven to get melem.

(2) The melem and the 3,3',4,4'-benzophenonetetracarboxylic dianhydride were placed in a quartz mortar and thoroughly ground to mix them evenly. The ground mixture was placed in a quartz boat and the quartz boat was placed in a tube furnace for heating. The gas in the quartz tube was replaced with nitrogen before heating to evacuate the air, and the nitrogen was always supplied during the heating. The tube furnace was heated to 300° C. at a heating rate of 5 K/min, and kept at this temperature for 4 h. After cooling, the sample was taken out of the tube furnace. Then, the obtained solid was washed three times with N,N-dimethylformamide and ethanol through vacuum filtration respectively, and the resulting solid was dried in a vacuum oven to get a final product.

According to an embodiment of the present invention, the heating rate of the muffle furnace in the step (1) is controlled at 1~10 K/min, the heating temperature is controlled at 400~500° C., and the obtained solid is washed with hot water of 60-80° C.

According to an embodiment of the present invention, the heating rate of the tube furnace in the step (2) is controlled at 1 to 10 K/min, and the heating temperature is controlled at 250 to 350° C., for example, 300° C.

The photocatalyst according to some embodiments of the present invention achieves energy level matching between the melem structure and the BTDA structure, reduces the singlet-triplet energy gap ($\Delta E_{ST}$), and promotes the intersystem crossing process, which is conducive to the production of singlet oxygen and to enhance its selective photocatalytic oxidation ability.

For the preparation method of the photocatalyst according to the embodiments of the present invention, there is no need to carry out complicated pretreatment and purification treatment, the raw material is cheaply available, simple and efficient to prepare, effective in environmental protection, and the batch preparation of high-efficiency selective photocatalyst can be realized.

DETAILED DESCRIPTION OF THE EMBODIMENTS

Figure 1:
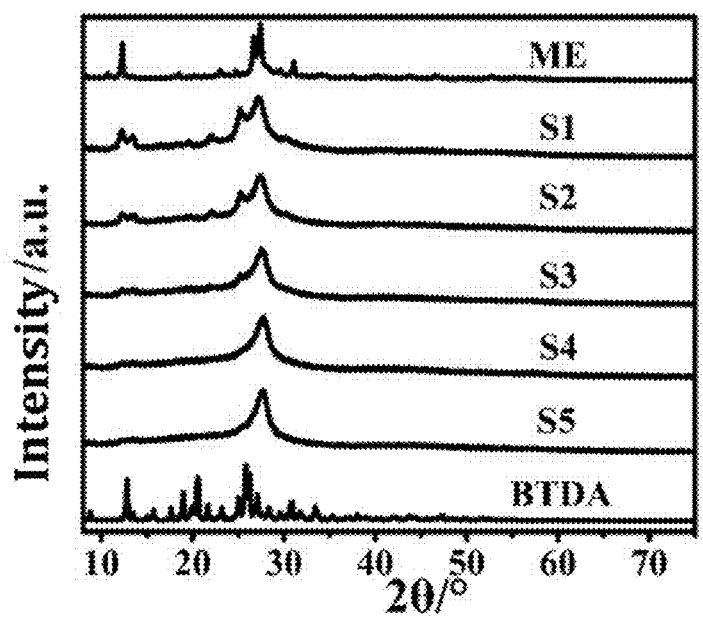
FIG. 1 shows X-ray diffraction spectra (XRD) of melem, 3,3',4,4'-benzophenonetetracarboxylic dianhydride and carbon nitride-based photocatalysts prepared in Examples 1 to 5.
Figure 2:
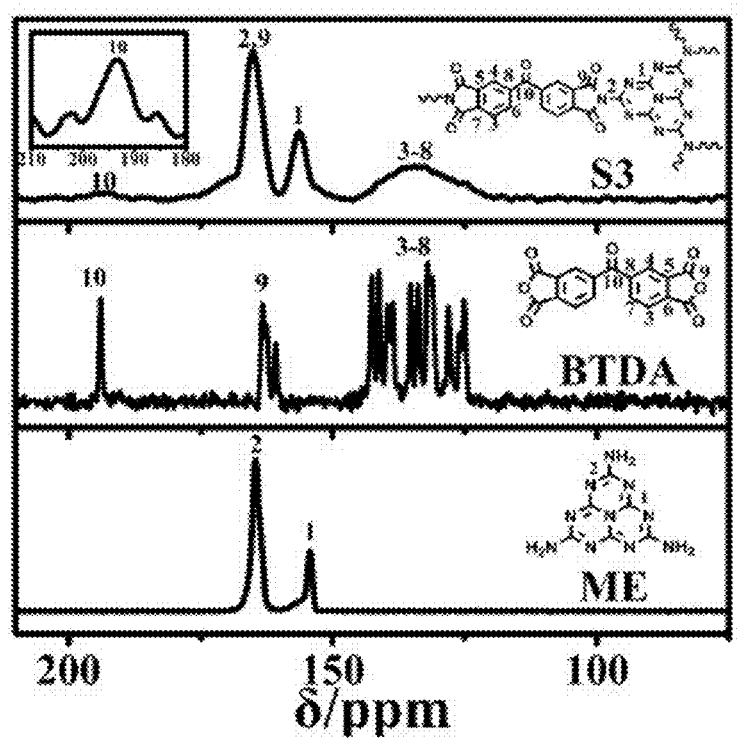
FIG. 2 shows solid nuclear magnetic $^{13}$C spectra ($^{13}$C-NMR) of melem, 3,3',4,4'-benzophenonetetracarboxylic dianhydride and carbon nitride-based photocatalyst prepared in Example 3.
Figure 3A:
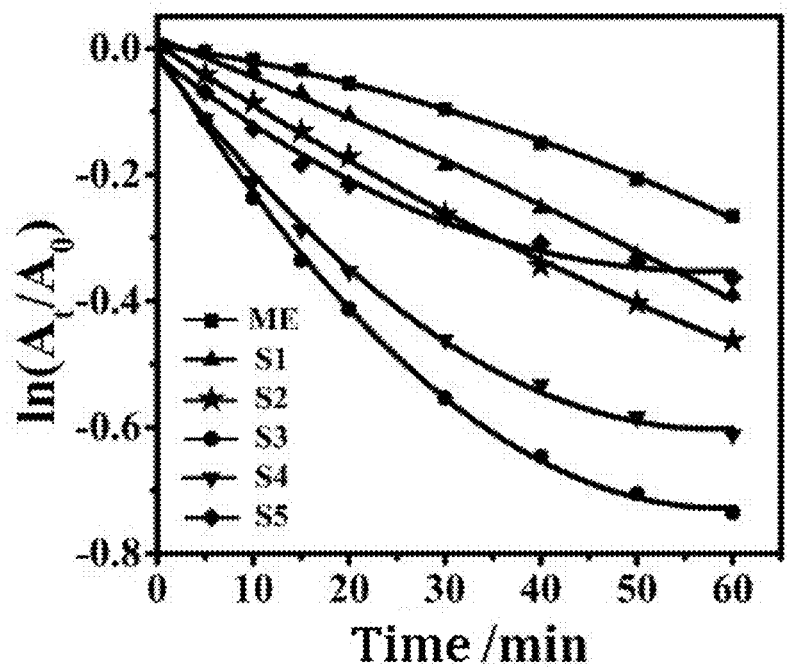
FIG. 3a shows a reaction rate of catalytic oxidation of 1,5-dihydroxynaphthalene by carbon nitride-based photocatalysts prepared in Examples 1 to 5 and melem.
Figure 3B:
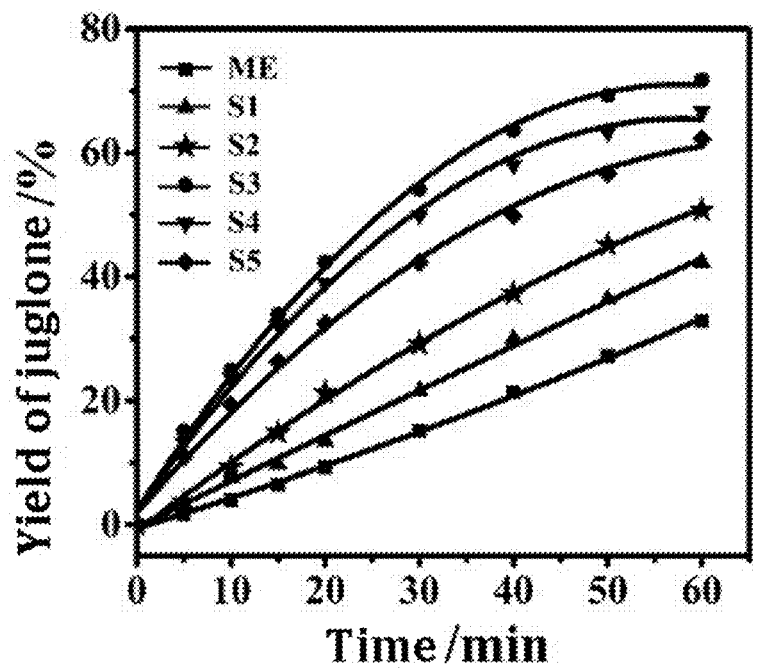
FIG. 3b shows the yield of juglone obtained by performing catalytic oxidation of 1,5-dihydroxynaphthalene with carbon nitride-based photocatalysts prepared in Examples 1 to 5.

Examples embodying the typical characteristics and advantages of the invention will be described below in detail. It shall be understood that various modifications may be made to different examples of the present invention without departing from the scope of protection of the present invention, and the descriptions herein are intended in essence to be explanatory and not to limit the invention.

The examples of the present invention provide a photocatalyst, of which a molecular structure includes a carbon nitride group, as shown below:

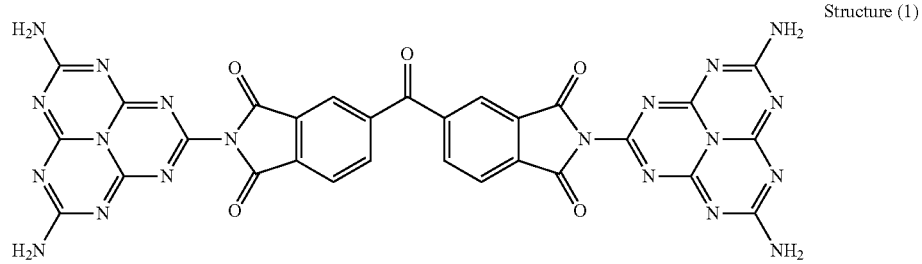 [SMILES: NC1=NC2=NC(N)=NC3=NC(N4C(=O)c5ccc(C(=O)c6ccc7c(c6)C(=O)N(C6=NC8=NC(N)=NC9=NC(N)=NC(=N6)N98)C7=O)cc5C4=O)=NC(=N1)N23]

Structure (1)

According to an embodiment of the present invention, the carbon nitride-based photocatalyst represented in the structure (1) is obtained by reacting melem with 3,3',4,4'-benzophenonetetracarboxylic dianhydride (BTDA).

One embodiment of the present invention provides a photocatalyst including a product obtained by reacting melem with 3,3',4,4'-benzophenonetetracarboxylic dianhydride.

Besides a compound represented by the structure (1), there may also be other products in the reaction product of melem and 3,3',4,4'-benzophenonetetracarboxylic dianhydride, and the structures of the products and the ratio of each structure will vary according to a molar ratio of the two reactants. In the above structure (1), one BTDA molecule is reacted with two melem molecules, and two anhydride groups in each BTDA molecule participate in the reaction, and only one amino group in each melem molecule participates in the reaction. In one embodiment of the present invention, two or three amino groups in each of the melem molecules may be simultaneously involved in the reaction to obtain a corresponding product; or only one anhydride group in the BTDA molecule may participate in the reaction. In addition, melem itself may undergo different degrees of condensation.

The photocatalyst according to an embodiment of the present invention achieves the energy level matching by combining a ketone carbonyl-containing structure (BTDA) with a carbon nitride structure (melem) by a chemical reaction, reduces the singlet-triplet energy gap (LEST), promotes the intersystem crossing process, thereby enhancing the singlet oxygen production and improving the selective photocatalytic oxidation ability.

The photocatalyst according to an embodiment of the present invention may produce $^1O_2$ under visible light irradiation, and can realize selective catalytic oxidation of 1,5-dihydroxynaphthalene; and at the same time, the photocatalyst is water-insoluble, and can realize heterogeneous catalysis. The products are easily separated from the system and the catalyst can be reused, which is of great value for the scale application of carbon nitride-based materials in the field of selective photocatalytic oxidation.

In one embodiment of the present invention, the melem may be prepared by the polymerization of melamine, and the photocatalyst is then prepared by reacting melem with 3,3',4,4'-benzophenonetetracarboxylic dianhydride. The photocatalyst prepared is free of precious metals, uses raw materials easily available, and features low cost, simple operation, and can be batch produced, which solves the application limitation of carbon nitride in the field of selective photocatalytic oxidation.

In an embodiment of the present invention, melem is prepared by polymerization of melamine at a temperature of 400~500° C., such as 425° C. or 450° C.

In an embodiment of the invention, melem can be prepared by the following steps:
placing the melamine-containing crucible in a muffle furnace, and raising the temperature of the muffle furnace to 425° C. at a heating rate of 1.77 K/min;
keeping the crucible at the above temperature of the muffle furnace for 4 h; and
preparing melem by removing the crucible from the muffle furnace and washing the obtained solid with water of 60~80° C.

In one embodiment of the present invention, the carbon nitride-based photocatalyst is obtained by reacting melem with 3,3',4,4'-benzophenonetetracarboxylic dianhydride at 250 to 350° C., for example, at 300° C. The reactivity of melem and 3,3',4,4'-benzophenonetetracarboxylic dianhydride is weak when the reaction temperature is lower than the above range; when the temperature is higher than the above range, 3,3',4,4'-benzophenonetetracarboxylic dianhydride volatilize seriously, resulting in the difficulty to get reaction products.

In one embodiment of the present invention, the molar ratio of melem and 3,3',4,4'-benzophenonetetracarboxylic dianhydride may be 5:1 to 1:10, for example, may be 3:1, 1:1 or 1:3.

In one embodiment of the present invention, melem and 3,3',4,4'-benzophenonetetracarboxylic dianhydride may react under the following conditions:
placing a quartz boat containing melem and 3,3',4,4'-benzophenonetetracarboxylic dianhydride in a tube furnace, and increasing the temperature of the quartz boat tube furnace to 300° C. at a heating rate of 5 K/min;
keeping the quartz boat at the above temperature for 4 h; and
taking the quartz boat out from the tube furnace, and washing the obtained solid with N,N-dimethylformamide and ethanol, respectively, to get the photocatalyst.

Further descriptions will be made below to a photocatalyst and a preparation method thereof according to one embodiment of the present invention with specific examples. The XRD, $^{13}$C-NMR and other tests involved are carried out under the following conditions.

XRD is commonly used to test a phase and a crystal form of a substance and a type of substance. An instrument used in the embodiments of the present invention is a PA's X'Pert Pro MPD type multi-crystal power X-ray Diffraction (XRD) with a tube voltage of 40 kV and a tube current of 40 mA, and the scan speed is 10° min$^{-1}$.

$^{13}$C-NMR is commonly used for the determination of molecular structure of organic matter. An instrument used in the embodiments of the present invention is a 400M wide-cavity solid-state nuclear magnetic resonance spectrometer of Bruker, Switzerland, which adopts a CP/MAS (cross-polarized magic angle rotation) BB/1H probe with a diameter of 4 mm, and the proton resonance frequency is 400 MHz. The melem and S3 relaxations are delayed by 3 s and the BTDA relaxation is delayed by 30 s.

The application example of the present invention utilizes the UV2700 ultraviolet visible spectrophotometer produced by Shimadzu Corporation of Japan, and the light absorbance of the prepared sample from 200 to 600 nm is tested. Based on Lambert Beer's law, the rate dependence curve is obtained by linear correlation between $\ln(A_0/A_t)$ and time according to the change of the UV absorption intensity of the substrate. According to the change of the ultraviolet absorption intensity of the product juglone, the yield of the juglone was calculated by the following formula:

$$\text{Juglone Yield} = \frac{100\ A_{final(Juglone)} / \varepsilon_{(Juglone)}}{C_{initiale(1,5-DHN)}}$$

In the above formula, $A_{final(Juglone)}$ is the final absorbance of the product juglone upon ending of reaction; $\varepsilon_{(Juglone)}$ is the molar extinction coefficient of juglone; $C_{initial(1,5-DHN)}$ is the initial concentration of 1,5-DHN.

The theoretical calculations were performed using Gaussian 09. The DFT calculation of the B3LYP/6-31G basis set is used to optimize the model structure, on the basis of which the energies of the singlet excited state and the triplet excited state are calculated. The energy gap between the singlet and the triplet is calculated by selecting the frontier molecular orbit (vibrator intensity, f≠0) of the singlet excited state and the triplet excited state.

3,3',4,4'-benzophenonetetracarboxylic dianhydride and melamine used in the Examples and Control Examples of the present invention were obtained from Aladdin Industrial Corporation. All the chemicals in our experiment were directly used without further purification.

Example 1

First, 10 g of melamine was weighed and placed evenly at the bottom of the crucible. The crucible was then placed in a muffle furnace, heated to 425° C. at a heating rate of 1.77 K/min, and held at this temperature for 4 h, and after cooling, a pale yellow solid was obtained. The obtained pale yellow solid was stirred in an appropriate amount of hot water (70° C.) for 15 min and vacuum-filtered three times, and the obtained solid was dried to get melem. 0.78 g of melem and 0.23 g of 3,3',4,4'-benzophenonetetracarboxylic dianhydride (the molar ratio of melem and BTDA were 5:1) were weighed and placed in a quartz mortar and ground uniformly to obtain a mixture. The mixture was then evenly spread in a quartz boat and placed in a tube furnace (under nitrogen atmosphere) for heating. The tube furnace was heated to 300° C. at a heating rate of 5 K/min, and kept at this temperature for 4 h. After cooling to a room temperature, the sample was taken out of the tube furnace to obtain a solid. Then, the obtained solid was washed three times with N,N-dimethylformamide and ethanol through vacuum filtration, respectively, and the resulting solid was dried in a vacuum drying oven to obtain a final product.

Example 2

First, 10 g of melamine was weighed and placed evenly at the bottom of the crucible. The crucible was then placed in a muffle furnace, heated to 425° C. at a heating rate of 1.77 K/min, and held at this temperature for 4 h to obtain a pale yellow solid, the obtained pale yellow solid was stirred in an appropriate amount of hot water (70° C.) for 15 min and vacuum-filtered three times to obtain a solid, the obtained solid was dried to get melem. 0.67 g of melem and 0.33 g of 3,3',4,4'-benzophenonetetracarboxylic dianhydride (the molar ratio of melem and BTDA were 3:1) were weighed and placed in a quartz mortar and ground uniformly to obtain a mixture. The mixture was then evenly spread in a quartz boat and placed in a tube furnace (under nitrogen atmosphere). The tube furnace was heated to 300° C. at a heating rate of 5 K/min, and kept at this temperature for 4 h. After cooling to the room temperature, the sample was taken out of the tube furnace to obtain a solid. Then, the obtained solid was washed three times with N,N-dimethylformamide and ethanol through vacuum filtration, respectively, and the resulting solid was dried in a vacuum drying oven to obtain a final product.

Example 3

First, 10 g of melamine was weighed and placed evenly at the bottom of the crucible. The crucible was then placed in a muffle furnace, heated to 425° C. at a heating rate of 1.77 K/min, and held at this temperature for 4 h and after cooling, a pale yellow solid was obtained. The obtained pale yellow solid was stirred in an appropriate amount of hot water (70° C.) for 15 min and vacuum-filtered three times to obtain a solid, the obtained solid was dried to get melem. 0.40 g of melem and 0.60 g of 3,3',4,4'-benzophenonetetracarboxylic dianhydride (the molar ratio of melem and BTDA were 1:1) were weighed and placed in a quartz mortar and ground uniformly to obtain a mixture. The mixture was then evenly spread in a quartz boat and placed in a tube furnace (under nitrogen atmosphere) for heating. The tube furnace was heated to 300° C. at a heating rate of 5 K/min, and kept at this temperature for 4 h. After cooling to the room temperature, the sample was taken out of the tube furnace to obtain a solid. Then, the obtained solid was washed three times with N,N-dimethylformamide and ethanol through vacuum filtration, respectively, and the resulting solid was dried in a vacuum drying oven to get a final product.

Example 4

First, 10 g of melamine was weighed and placed evenly at the bottom of the crucible. The crucible was then placed in a muffle furnace, heated to 425° C. at a heating rate of 1.77 K/min, and held at this temperature for 4 h, and after cooling, a pale yellow solid was obtained. The obtained pale yellow solid was stirred in an appropriate amount of hot water (70° C.) for 15 min and vacuum-filtered three times to obtain a solid, the obtained solid was dried to get melem. 0.18 g of melem and 0.82 g of 3,3',4,4'-benzophenonetetracarboxylic dianhydride (the molar ratio of melem and BTDA were 1:3) were weighed and placed in a quartz mortar and ground uniformly to obtain a mixture. The mixture was then evenly spread in a quartz boat and placed in a tube furnace (under nitrogen atmosphere). The tube furnace was heated to 300° C. at a heating rate of 5 K/min, and kept at this temperature for 4 h. After cooling to the room temperature, the sample was taken out of the tube furnace to obtain a solid. Then, the obtained solid was washed three times with N,N-dimethylformamide and ethanol through vacuum filtration respectively, and the resulting solid was dried in a vacuum drying oven to obtain a final product.

Example 5

First, 10 g of melamine was weighed and placed evenly at the bottom of the crucible. The crucible was then placed in a muffle furnace, heated to 425° C. at a heating rate of 1.77 K/min, and held at this temperature for 4 h, and after cooling, a pale yellow solid was obtained. The obtained pale yellow solid was stirred in an appropriate amount of hot water (70° C.) for 15 min and vacuum-filtered three times to obtain a solid, the obtained solid was dried to get melem. 0.12 g of melem and 0.88 g of 3,3',4,4'-benzophenonetetracarboxylic dianhydride (the molar ratio of melem and BTDA were 1:5) were weighed and placed in a quartz mortar and ground uniformly to obtain a mixture. The mixture was then evenly spread in a quartz boat and placed in a tube furnace (under a nitrogen atmosphere). The tube furnace was heated to 300° C. at a heating rate of 5 K/min, and kept at this temperature for 4 h. After cooling to the room temperature, the sample was taken out of the tube furnace to obtain a solid. Then, the obtained solid was washed three times with N,N-dimethylformamide and ethanol through vacuum filtration respectively, and the resulting solid was dried in a vacuum drying oven to obtain a final product.

Control Example 1

0.28 g of melamine and 0.72 g of 3,3',4,4'-benzophenonetetracarboxylic dianhydride (the molar ratio was 1:5) were weighed and placed in a quartz mortar and ground uniformly to obtain a mixture. The mixture was then evenly spread in a quartz boat and placed in a tube furnace (under nitrogen atmosphere). The tube furnace was heated to 300° C. at a heating rate of 5 K/min, and kept at this temperature for 4 h. After cooling to the room temperature, the sample was taken out of the tube furnace to obtain a solid. Then, the obtained solid was washed three times with N,N-dimethylformamide and ethanol through vacuum filtration respectively, and the resulting solid was dried in a vacuum drying oven to get a final product.

Control Example 2

First, 10 g of melamine was weighed and placed evenly at the bottom of the crucible. The crucible was then placed in a muffle furnace, and heated to 425° C. at a heating rate of 1.77 K/min, then held at this temperature for 4 h, and after cooling, a pale yellow solid was obtained. The obtained pale yellow solid was stirred in an appropriate amount of hot water (70° C.) for 15 min and vacuum-filtered three times to obtain a solid, and the obtained solid was dried to get melem. 0.43 g of melem and 0.57 g of 3,3',4,4'-biphenyltetracarboxylic dianhydride (the molar ratio was 1:1) were weighed and placed in a quartz mortar and ground uniformly to obtain a mixture. The mixture was then evenly spread in a quartz boat and placed in a tube furnace (under a nitrogen atmosphere). The tube furnace was heated to 300° C. at a heating rate of 5 K/min, and kept at this temperature for 4 h. After cooling to the room temperature, the sample was taken out of the tube furnace to obtain a solid. Then, the obtained solid was washed three times with N,N-dimethylformamide and ethanol through vacuum filtration respectively, and the resulting solid was dried in a vacuum drying oven to obtain a final product.

The products obtained in Examples 1 to 5, Control Examples 1, 2 and melem were used as photocatalysts for catalytically oxidizing 1,5-dihydroxynaphthalene according to the following steps, and the relevant data measured are shown in the following table.

Application Example

200 µL of 1,5-dihydroxynaphthalene ($10^{-2}$ mol/L) and 20 mg of the prepared photocatalyst were added into a round bottom flask containing 20 mL of a mixed solution of acetonitrile and water (v/v=5:1), stirred continuously at room temperature and air atmosphere, and a 35 W xenon lamp ($\lambda$>380 nm) was used to illuminate at a light intensity of 600 W/m$^2$. Samples were taken at intervals of 10 min, centrifuged, and the supernatant was filtered through a 0.45 µm syringe filter. The change of the absorbance of 1,5-dihydroxynaphthalene at 331 nm and the change of the absorbance of the product juglone at 425 nm were measured by UV-Vis spectrophotometer. The reaction time (60 minutes) of the example 3 with best effect was taken as a standard, and reactions in the other examples and the control examples were all stopped after 60 minutes. The measured yield of the juglone was as shown in the following table.

| | S1 | S2 | S3 | S4 | S5 | Control Example 1 | Control Example 2 |
|---|---|---|---|---|---|---|---|
| Juglone yield (%) | 42.33 | 50.74 | 71.77 | 66.72 | 62.24 | 37.57 | 24.39 |

The photocatalyst in the Control Example 1 was directly prepared by using melamine as a reactant to react with BTDA. In the reaction of catalyzing 1,5-dihydroxynaphthalene, the yield of the obtained juglone was much lower than that by the photocatalyst in the examples of the present invention. The photocatalyst in the Control Example 2 was prepared by reacting 3,3',4,4'-biphenyltetracarboxylic dianhydride (similar to BTDA in structure) with melem. In the reaction of 1,5-dihydroxynaphthalene catalyzed by Control Example 2, the juglone yield was also much lower than that by the photocatalyst in the examples of the present invention.

FIGS. 1 to 3b show relevant data for Examples 1 to 5, melem and BTDA of the present invention, wherein ME represents melem, and S1, S2, S3, S4, and S5 represent the photocatalysts in Examples 1 to 5, respectively. It can be seen from the data in FIG. 1 that the photocatalyst has characteristic diffraction peaks of melem and 3,3',4,4'-benzophenonetetracarboxylic dianhydride after the reaction, indicating that melem successfully reacted with 3,3',4,4'-benzophenonetetracarboxylic dianhydride. The solid nuclear magnetic data of FIG. 2 also demonstrates this point. In addition, the signal attributed to the ketone carbonyl carbon atom was still present at 194 ppm in the prepared photocatalyst, indicating that the benzophenone structure was not destroyed after the reaction, which was one of the reasons why the prepared photocatalyst shows better photocatalytic ability.

Figure 4A:
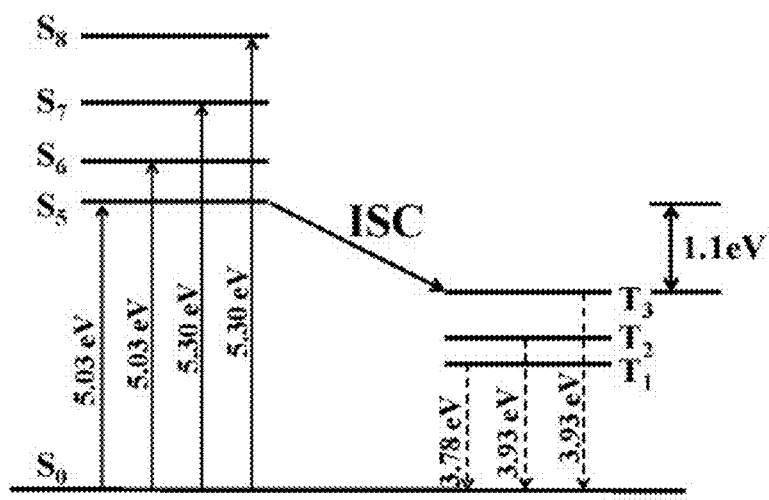
FIG. 4a is an energy level diagram of melem.
Figure 4B:
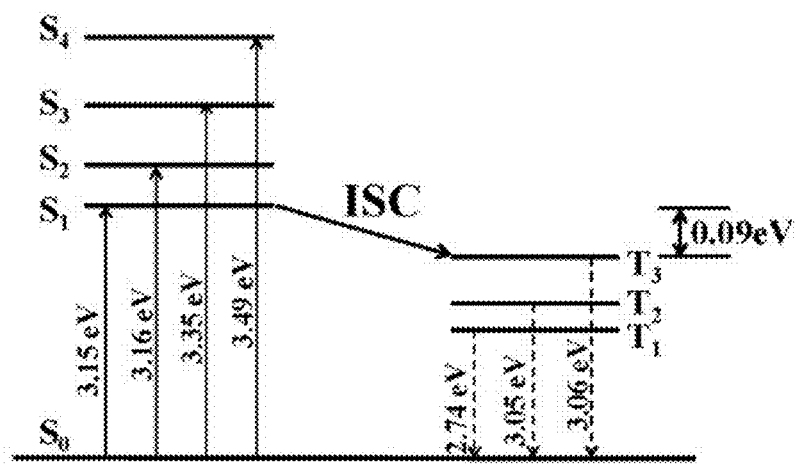
FIG. 4b is an energy level diagram of photocatalyst prepared in Example 3.

The photocatalysts prepared in Examples 1 to 5 were used for catalytic oxidation of 1,5-dihydroxynaphthalene, and the reaction rate (FIG. 3a) and the juglone yield (FIG. 3b) showed that the photocatalytic effects of the prepared photocatalysts were promoted. The photocatalyst obtained in Example 3 has the best catalytic effect, and the yield of the juglone can reach 71.77%. The energy level diagrams of FIGS. 4a and 4b are obtained by Gaussian theory calculation. The singlet-triplet energy gap of the photocatalyst obtained in Example 3 (0.09 eV) is much smaller than that of the raw material melem (1.1 eV). The smaller singlet-triplet energy gap can effectively promote the intersystem crossing (ISC) process, enhance the production of singlet oxygen, and thus improve the catalytic effect.

Unless otherwise specified, the terms used in the present invention have the meanings as commonly understood by technicians in the field.

The embodiments described in the present invention are only for illustrative purposes and are not intended to limit the scope of protection of the present invention. Various other substitutions, changes and improvements may be made by technical personnel in the art within the scope of the present invention. Therefore, the present invention is only limited by the claims rather than the above embodiments.

The invention claimed is:

1. A carbon nitride photocatalyst prepared by reacting melem with 3,3',4,4'-benzophenonetetracarboxylic dianhydride.

2. The carbon nitride photocatalyst according to claim 1, wherein a molar ratio of melem to the 3,3',4,4'-benzophenonetetracarboxylic dianhydride is 5:1~1:5.

3. A carbon nitride photocatalyst having the following structure:

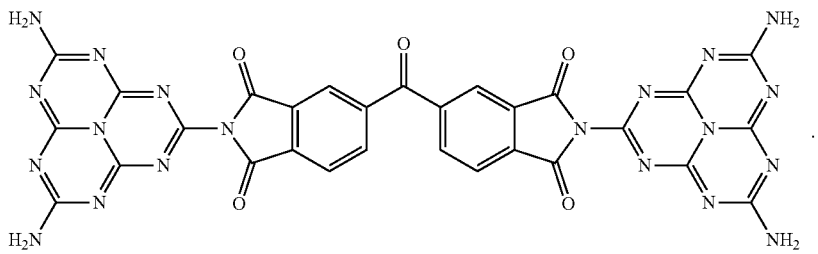 [SMILES: NC1=NC2=NC(N)=NC3=NC(N4C(=O)c5ccc(C(=O)c6ccc7c(c6)C(=O)N(C6=NC8=NC(N)=NC9=NC(N)=NC(=N6)N98)C7=O)cc5C4=O)=NC(=N1)N23]

4. A method for preparing a carbon nitride photocatalyst, comprising:
preparing melem by polymerization of melamine; and
obtaining the carbon nitride photocatalyst by reacting the melem with the 3,3',4,4'-benzophenonetetracarboxylic dianhydride.

5. The method according to claim 4, wherein the melamine was polymerized at a temperature of 400~500° C.

6. The method according to claim 5, comprising:
placing a melamine-containing crucible in a muffle furnace, and raising the temperature of the muffle furnace to 425° C. at a heating rate of 1.77 Kelvin (K)/min;
keeping the crucible at the above temperature for 4 hours (h); and
preparing the melem by removing the crucible from the muffle furnace and washing an obtained solid with water of 60~80° C.

7. The method according to claim 4, wherein the molar ratio of the melem to the 3,3',4,4'-benzophenonetetracarboxylic dianhydride is 5:1~1:5.

8. The method according to claim 7, wherein the molar ratio of the melem to the 3,3',4,4'-benzophenonetetracarboxylic dianhydride is 1:1.

9. The method according to claim 4, wherein the carbon nitride photocatalyst was obtained by reacting the melem with the 3,3',4,4'-benzophenonetetracarboxylic dianhydride at 250 to 350° C.

10. The method according to claim 9, wherein a quartz boat containing the melem and the 3,3',4,4'-benzophenonetetracarboxylic dianhydride was placed in a tube furnace, and the temperature of the tube furnace was increased to 300° C. at a heating rate of 5 Kelvin (K)/min;
the quartz boat was kept at the above temperature for 4 hours (h); and
the quartz boat was taken out from the tube furnace to obtain a solid, and the obtained solid was washed with N,N-dimethylformamide and ethanol respectively, to get the photocatalyst.

* * * * *